(12) United States Patent  (10) Patent No.: US 8,501,222 B2
Mythen  (45) Date of Patent: *Aug. 6, 2013

(54) ORAL CARE AND DELIVERY DEVICE

(75) Inventor: Daniel Richard Mythen, Redmond, WA (US)

(73) Assignee: Daniel Richard Mythen, Redmond, WA (US)

( * ) Notice: Subject to any disclaimer, the term of this patent is extended or adjusted under 35 U.S.C. 154(b) by 23 days.

This patent is subject to a terminal disclaimer.

(21) Appl. No.: 13/094,797

(22) Filed: Apr. 26, 2011

(65) Prior Publication Data

US 2011/0200972 A1  Aug. 18, 2011

Related U.S. Application Data

(63) Continuation-in-part of application No. 11/553,620, filed on Oct. 27, 2006, now Pat. No. 7,931,913, which is a continuation-in-part of application No. 11/093,785, filed on Mar. 29, 2005, now Pat. No. 7,592,018.

(51) Int. Cl.
*A61K 9/68* (2006.01)

(52) U.S. Cl.
USPC .............................................. 424/440

(58) Field of Classification Search
None
See application file for complete search history.

(56) References Cited

U.S. PATENT DOCUMENTS

| | | | | |
|---|---|---|---|---|
| 6,004,334 A * | 12/1999 | Mythen | ........................ | 606/161 |
| 7,592,018 B2 * | 9/2009 | Mythen | ........................ | 424/440 |
| 7,931,913 B2 * | 4/2011 | Mythen | ........................ | 424/440 |

* cited by examiner

*Primary Examiner* — Carlos Azpuru
(74) *Attorney, Agent, or Firm* — Dergosits & Noah LLP

(57) ABSTRACT

A device for providing oral care. The device is formed to have surface features for delivery of medication or other compositions to the mouth, the throat, the gums and the cheeks. Blisters or cavities are formed on a surface of the device to contain and deliver a material, such as mouthwash or medicine, into the various areas of the mouth of the user, and may be formed to provide a time-controlled release of the deliverable material.

13 Claims, 4 Drawing Sheets

FIG 1a
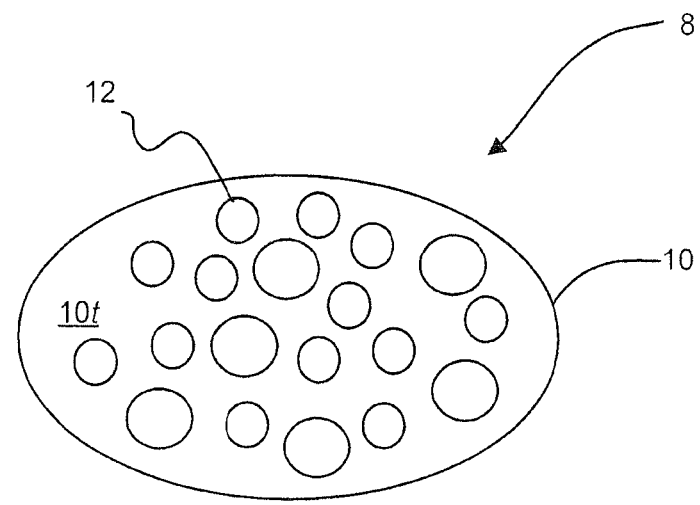
FIG 1b
FIG 1c
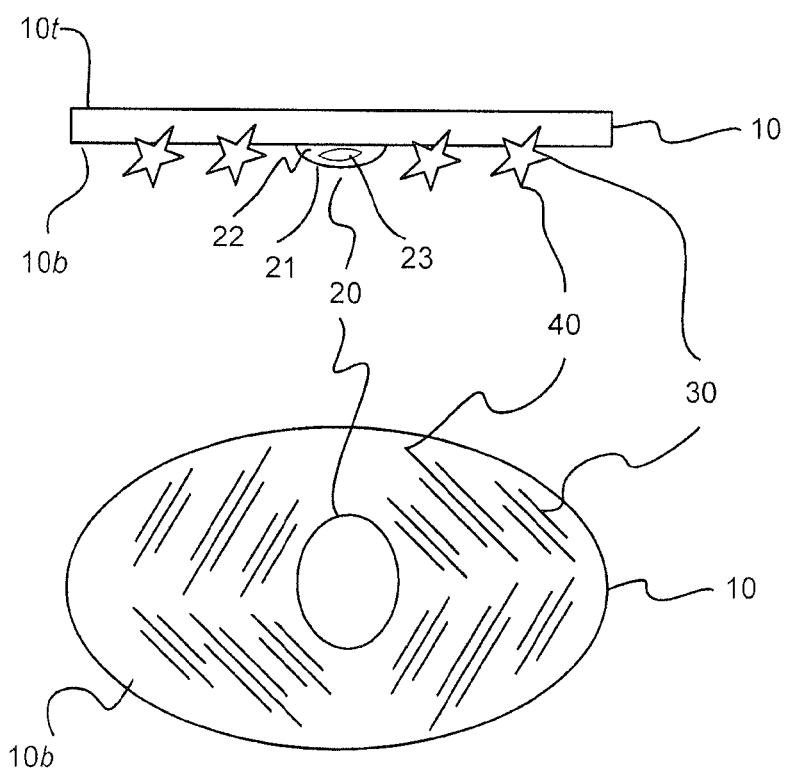

ORAL CARE AND DELIVERY DEVICE

CROSS-REFERENCE TO RELATED APPLICATIONS

This application is a continuation-in-part of U.S. patent application Ser. No. 11/553,620, filed Oct. 27, 2006, which was a continuation-in-part of U.S. patent application Ser. No. 11/093,785, filed Mar. 29, 2005.

BACKGROUND

The present disclosure relates generally to devices for cleaning the tongue and mouth and/or delivering pharmaceutical compositions or other treatments to various areas of the mouth.

Oral malodor, also known as bad breath or halitosis, is a common condition afflicting many people. The origin of oral malodor may be physiological or pathological in nature. However, even for individuals having healthy periodontal tissues and practicing good oral hygiene, the back of the tongue is a significant source of oral malodor due to the production of volatile sulfur compounds.

Various devices are known for addressing oral malodor. For example, U.S. Pat. No. 5,226,197 discloses a tongue hygiene device shaped like a toothbrush but with a wider than normal head, short bristles and a scraper. U.S. Pat. No. 6,004,334 discloses an edible confection having a soft side and a hard side, wherein the hard side has a raised pattern to help scrape the tongue. However, it remains desirable to find useful solutions that help to fight oral malodor.

SUMMARY

A device is formed to provide effective cleaning and tongue-scraping action, and/or to deliver modest amounts of a material, such as mouthwash or medicine. The device is preferably a soft pliable edible dissolvable confection formed to have beneficial surface features.

In one embodiment, the device is lozenge-shape and formed of a base material having one or more surface features. A plurality of depressions are formed on one surface of the device to facilitate adhering the device to the roof of the mouth, and a plurality of hard candy segments are formed on another surface of the device. Preferably, the segments have raised ridges which are suitable for abrading the tongue.

In one embodiment, the depressions may be used as cavities to allow the user to fill the cavities with a desired deliverable material.

In one embodiment, the cavities have walls to form blisters on a surface to deliver a material, such as a pharmaceutical composition or other beneficial treatment.

In use, the device is adhered to the roof of the mouth and the user's tongue passes over the hard candy segments formed in the soft candy. Preferably, the soft candy is repeatedly removed and adhered in a new spot to permit more thorough coverage of the tongue until the candy is dissolved. Further, the blisters dissolve to deliver a material to the user's tongue. Advantageously, the blisters may have varying dissolve rates based on different wall thicknesses so that a time-controlled release of the material can be provided. Alternatively, the blisters may be formed of an absorbable surgical suture material that encapsulates the desired deliverable materials.

In one embodiment, the device is formed as a thin rectangular shape of a base material having one or more surface features for providing delivery of desired materials to the various regions of the mouth.

A better understanding of the features and advantages of the present invention will be obtained by reference to the following detailed description and accompanying drawings which set forth an illustrative embodiment in which the principles of the invention are utilized.

BRIEF DESCRIPTION OF THE DRAWINGS

FIG. 1a is a top plan view of one embodiment of an oral care device.

FIG. 1b is a side plan view of the device of FIG. 1a.

FIG. 1c is a bottom plan view of the device of FIG. 1a.

DETAILED DESCRIPTION

The present disclosure describes a device that is suitable for oral use to clean and disinfect portions of the oral cavity, including the mouth, the throat, the gums and the cheeks, and/or to deliver pharmaceutical compositions or other treatments to these areas. In particular, surfaces of the device can be augmented to add a variety of features that provide oral care benefits for cleaning and/or disinfecting the tongue, the mouth the gums and the cheeks. In one embodiment, depressions may be formed in the surface to provide "suction cups" that help the device adhere to the roof of the mouth. In another embodiment, the depressions are cavities that may be used to contain a deliverable material, such as mouthwash or medicine, to the mouth cavity. In yet another embodiment, the cavities have walls to form blisters in the surface to contain and provide the deliverable material. Advantageously, the blisters can be designed to dissolve at different rates, thus providing a timed-release control mechanism. In one embodiment, the blisters are formed from a surgical suture material that encapsulates a deliverable material, and upon use, dissolves and is absorbed into the body of the user. However, it should be recognized that these and other features could have many shapes and sizes, and could be combined to suit particular applications. Thus, the embodiments described herein are merely illustrative and not limiting.

Figure 2:
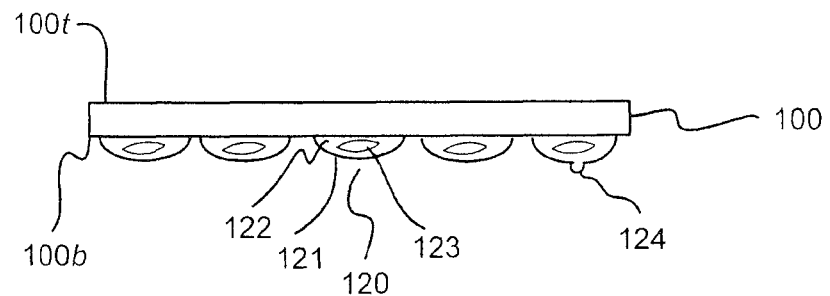
FIG. 2 is a side plan view of another embodiment of a oral care device.
Figure 3:
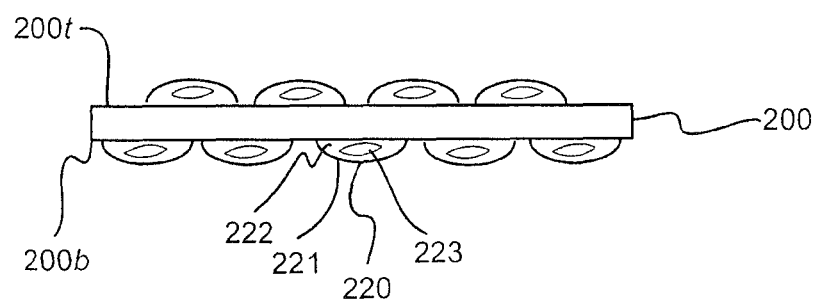
FIG. 3 is a side plan view of yet another embodiment of a oral care device.

FIGS. 1-3 show an oval-shaped device 8 having a main body 10 formed of a base material, preferably a soft, edible confection, such as used in GUMMI-BEAR or GUMMI-WORM type confections. Other materials could also be used, including gelatinous or gum-based materials, such as sodium alginate. Further, additional materials could be added to the base material to provide additional benefits, such as masking additives, zinc glutonate, sweeteners, etc. For example, a dentifrice could be added to the base material to provide a tooth cleaning polish that can act while the user chews or sucks on the device. The preferred overall length L of the device is approximately 1 inch to 1¾ inch, while the preferred overall the width W is approximately ¾ inch to 1 inch. The preferred thickness T of the device 10 is approximately ⅛ inch to ⅜ inch.

The top surface 10t of device 10 is generally smooth, but small circular depressions 12 (resembling suction cups) are formed in the surface. In a preferred embodiment, each depression measures approximately ⅛ inch to ⅜ inch in diameter and 1/64 inch to 1/32 inch deep. The depressions 12 assist the device in adhering firmly to the roof and soft palate of the mouth by a suction effect while the tongue moves across the bottom side 10b of the device. The suction cup depressions 12 may be formed in any type of pattern or randomly across the top surface 10t of the device.

The bottom surface 10b of device 10 is imbedded with hard segments 30 and at least one generally circular blister 20. Each of the hard segments 30 is preferably a hard dissolvable confection, such as hard peppermint candy, which can be formed using conventional confectionery methods to define a pattern, such as by extruding, molding or stamping. For example, in this embodiment, each segment 30 is approximately ⅛ inch to ⅜ inches long and ⅛ inches wide with raised scraping ridges 40, and forms a five-point star pattern defined by ridges 40 which extend from the surface 10b of the soft candy body by approximately /1;16 inch. The ridges 40 provide a rigid scraping surface that abrades the tongue as it passes along the device, which is adhered to the roof of the mouth. Other patterns with more ridges may prove equally effective.

In one embodiment, the blister 20 is formed using conventional confectionery techniques to have a wall 21 that encloses a cavity 22. The cavity 22 is filled with a liquid, solid, or semi-solid material 23, such as a freshening and/or disinfecting agent, for example, mouthwash including chlorohexadine, which is released onto the tongue as the wall of the blister dissolves.

In another embodiment, the blister could be formed using an absorbable surgical suture material, such as polyglycolic acid, polylactic acid, or polydioxanone. For example, a pillow-like structure can be formed from the suture material to contain the deliverable. Further, the suture material may be specified to have different absorption or dissolve rates.

In yet another embodiment, the blister 20 does not have a wall 21, but just the cavity 22, and material may be added to the cavity by the user. For example, a user may obtain a prescription for a deliverable medicine in a paste, gel, cream or powder form, and fill the cavity themselves, for example using a small spatula or butter knife, or from an ampule having a premeasured dose.

In use, the device 10 may be repeatedly removed and reapplied to different positions in the mouth. By moving the position of the device in the mouth, a more thorough coverage of the tongue by the abrasive scraping action of the device is provided. Such action may be repeated until the scraping surface is fully dissolved.

In another embodiment, shown in FIG. 2, device 100 includes multiple blisters 120 formed on the bottom face 10b of the device, but no hard segments. Enclosed within each of the blisters 120 is a deliverable material 123, which is delivered onto the user's tongue as the walls 121 of the blisters dissolve. For example, pharmaceutical compositions, including antibiotics, disinfectants, and freshening agents, could be enclosed within the blisters 120 to treat the mouth in general, or targeted to treat specific portions of the mouth, such as the soft palette, tongue or cheeks. As another example, pieces of hard peppermint candy or similar could be provided, loose or attached, within at least some of the blisters 120. Further, a dentifrice could be provided within the blisters to provide a tooth polishing feature.

The walls 121 of blisters 120 could be formed with different thicknesses on the same device 100 in order to provide a time release control for delivery of material 123. Likewise, different devices could be specified for particular applications, with blisters and walls sized varying according to need. A device could be designed having blisters with suitable wall thicknesses to discharge a sore throat medication at intervals of three, five and ten minutes. Another device could be designed having blisters with suitable wall thicknesses to continuously discharge a medication for treating oral yeast infection for thirty seconds or longer. In one embodiment, a small nipple 124 could be formed in the center of a blister 120 that, when dissolved, allows a slow continuous flow of liquid from the blister. For example, chlorohexadine is an effective medication for treating infection, but is quickly dissolved in saliva thereby limiting its effectiveness for oral use. By providing a device with blisters designed for timed or continuous release control, chlorohexadine can be used more effectively for oral treatments.

Alternatively, the blisters could be formed of a absorbable surgical suture material as described above. Thus, the suture encapsulates an antimicrobial substance or other medicinal composition for delivery to the user as the suture dissolves. For example, the suture material could be formed into a pillow shape and embedded into the cavity during manufacture of the device.

In yet another embodiment, the blister 20 does not have a wall 21, but just the cavity 22, and the deliverable material may be added to the cavity by the user. For example, a user may obtain a prescription for a deliverable medicine or other systemic treatment in a paste, gel, cream or powder form, and fill the cavity themselves, for example using a small spatula or butter knife, or from an ampule having a premeasured dose.

In yet another embodiment, shown in FIG. 3, device 200 includes multiple blisters 220 formed on both the top face 200t and the bottom face 200b of the device. Enclosed within each of the blisters 220 is a deliverable material 223, which is delivered to the user as the walls 221 of the blister dissolve. As can be appreciated, many types of devices can be specified to deliver a particular material, where suction cups and blisters can be formed in a variety of configurations.

Figure 4:
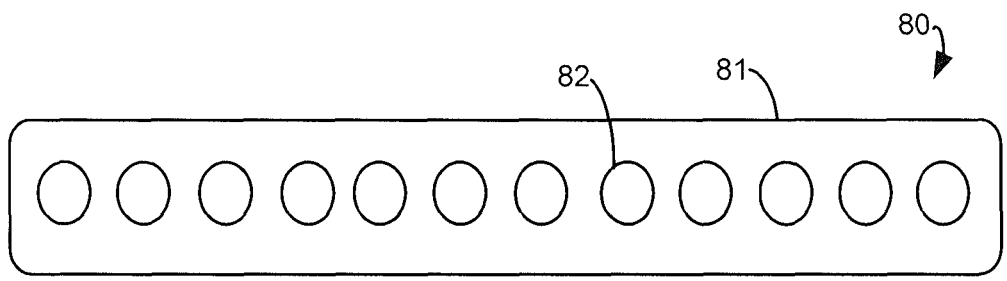
FIG. 4 is a top plan view of an embodiment of an oral care device.

FIG. 4 illustrates another embodiment, wherein a rectangular-shaped device 80 has a main body 81 formed of a base material, preferably a dissolvable edible confection. Gelatinous or gum-based materials, such as sodium alginate, could also be used. Other non-dissolvable materials, such as plastic or wax, could be used, but are less preferred. Further, additional materials could be added to the base material to provide additional benefits, such as taste masking additives, zinc glutonate, sweeteners, dentifrice, etc. The preferred overall length L of the device is approximately 2-3 inches, while the preferred overall the width W is approximately ¼ inch to ¾ inch, and the preferred thickness T of the device 10 is approximately 1/32 inch to ⅛ inch.

The surface of device 80 is generally smooth, but has one or more small circular cavities 82 formed therein. In a preferred embodiment, each cavity 82 measures approximately ⅛ inch to ⅜ inch in diameter and 1/64 inch to 1/32 inch deep. The cavity 82 may be formed in any type of pattern or randomly across the surface of the device. Each cavity may be filled with a deliverable material as described above. For example, a user may obtain a deliverable material and fill the cavities themselves as described above. Alternatively, instead of cavities, blisters may be formed on the surface and prefilled with a deliverable material at the time of manufacture as described above.

In use, the device 80 may be placed along the gum line between the teeth and lips, such that medicine or other deliverable material may be provided to that area.

Figure 5A:
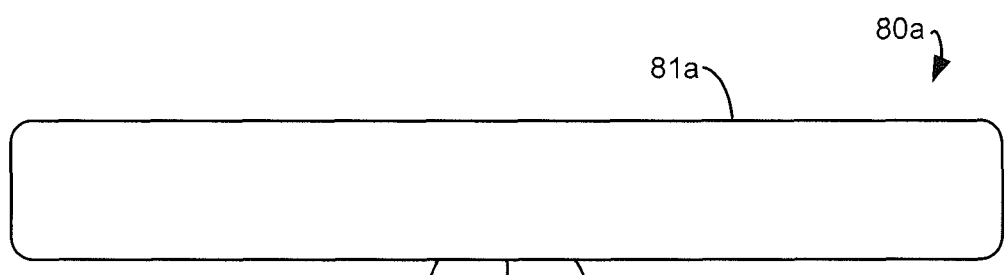
FIG. 5A is a top plan view of an embodiment of an oral care device.

Another alternative is shown in FIG. 5, wherein device 80a includes base material 81a with a fully integrated tab 85 formed to hang down from a central portion of the device. The tab 85 has one or more cavities or blisters 82a formed thereon for providing deliverable materials as described above. As shown, a single cavity or blister 82a is provided that is larger than those described above, for example, up to ⅝ inch. In use, the device is placed against the inside of the bottom teeth of the user and the tab portion 85 rests under the tongue for sublingual delivery of material with the blisters or cavities. In one embodiment, the tab 85 and cavity 82a may include a cleave 84 (shown in dashed lines) in the middle to better accommodate the central tissue on the underside of the tongue.

In one variation, the device 80a could also include one or more cavities or blisters formed across the length of the base material, as previously described and shown in FIG. 4.

Figure 5B:
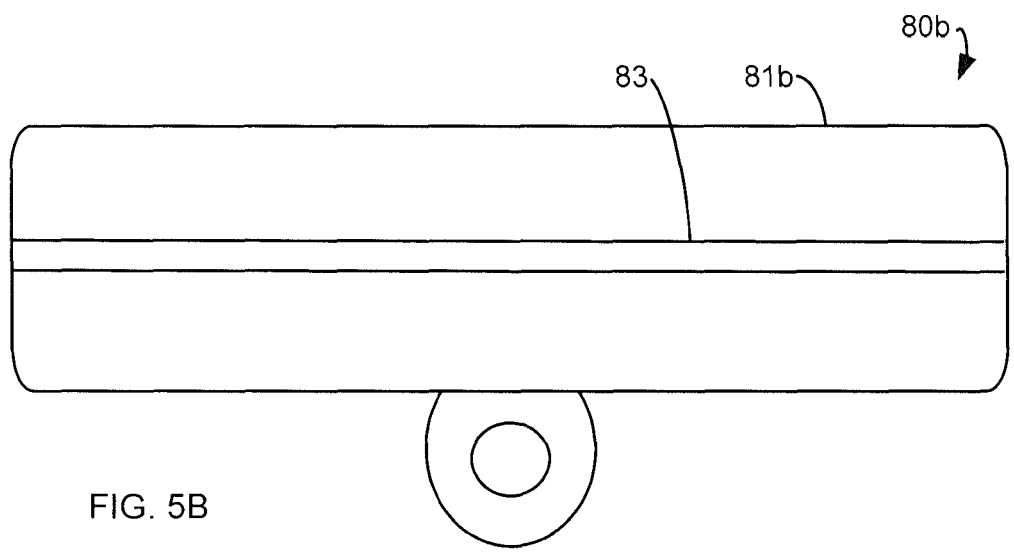
FIG. 5B is a top plan view of an embodiment of an oral care device.

Another variation is shown in FIG. 5B, wherein for device 80b, the base material 81b is approximately twice as wide as previously described, and includes a fold line 83 through the middle of the length of the device. In use, the device 80b may be folded over the teeth at the fold line 83 into a U-shape or a V-shape to better hold the device in place and/or to provide deliverable material to the front and back of the teeth and gums via the rectangular portion of the base material as well as sublingual delivery through the tab portion.

Figure 6A:
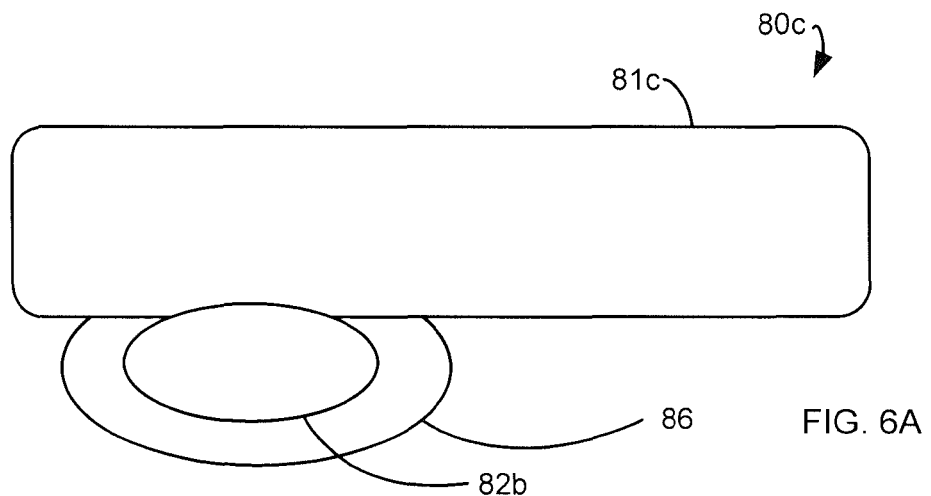
FIG. 6A is a top plan view of an embodiment of an oral care device.

Yet another alternative is shown in FIG. 6A, wherein for device 80c, the base material 81c has a tab 86 formed to hang down from a portion of the device near the end of its length. The tab 86 has one or more cavities or blisters 82b formed thereon for providing deliverable materials as described above. As shown, a single cavity or blister 82b is provided that may be larger than those described with regard to FIG. 5A (since the cheek area is larger), for example, up to ¾ inch or more. In use, the device is placed against the outside of the bottom teeth of the user and the tab portion 86 rests against the cheek for buccal delivery of material with the blisters or cavities.

In a variation, the device 80c could also include one or more cavities or blisters formed across the length of the base material, as previously described and shown in FIG. 4.

Figure 6B:
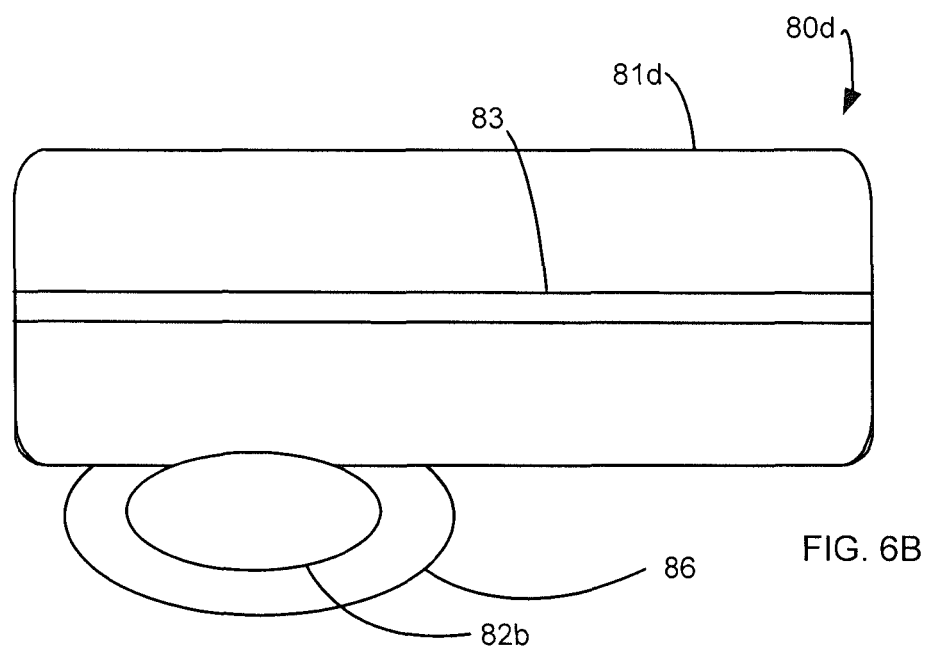
FIG. 6B is a top plan view of an embodiment of an oral care device.

Another variation is shown in FIG. 6B, wherein for device 80d, the base material 81d is approximately twice as wide as previously described, and as in FIG. 5B includes a fold line 83 through the middle of the length of the device. In use, the device 80d may be folded over the teeth to better hold the device in place and/or to provide deliverable material to the front and back of the teeth and gums as well as buccal delivery.

Although the subject matter has been described in language specific to structures and/or methods, it should be understood that the subject matter defined in the appended claims is not necessarily limited to the specific structures or methods described above. Rather, the specific structures or methods described above are disclosed as example forms of implementing the claims. For example, dimensions and materials are specified for the described embodiments, but many variations will be obvious to one with skill in such matters.

I claim:

1. An oral care and delivery apparatus, comprising:
   a soft, edible base material formed into a shape suitable for oral use; and
   at least one surface feature formed on the base material for providing a deliverable material to a user, said surface feature dissolving or absorbing into the user's body upon use.

2. The apparatus of claim 1, wherein the base material is a thin rectangular shape sized to be used adjacent the teeth of a user.

3. The apparatus of claim 2, wherein the surface feature is a plurality of blisters formed on the base material, said blisters containing the deliverable material.

4. The apparatus of claim 2, wherein the surface feature is a plurality of cavities formed on the base material, said cavities containing the deliverable material.

5. The apparatus of claim 2, wherein the base material includes a tab extending from a portion of the thin rectangular shape, and wherein the surface feature is at least one blister formed on the tab of the base material, said blister containing the deliverable material.

6. The apparatus of claim 2, wherein the base material includes a tab extending from a portion of the thin rectangular shape, and wherein the surface feature is at least one cavity formed on the tab of the base material, said cavity containing the deliverable material.

7. The apparatus of claim 5, wherein the tab extends from a central portion of the base material.

8. The apparatus of claim 6, wherein the tab extends from a central portion of the base material.

9. The apparatus of claim 5, wherein the tab extends from an end portion of the base material.

10. The apparatus of claim 6, wherein the tab extends from an end portion of the base material.

11. The apparatus of claim 1, wherein the base material is a thin rectangular shape having a fold line thereby allowing the base material to be folded over the teeth of a user such that the base material abuts both the front and back of the user's teeth.

12. The apparatus of claim 3, wherein the blisters are formed from surgical suture material to contain the deliverable material.

13. An oral care and delivery apparatus, comprising:
    a base material formed into a thin rectangular shape having a fold line thereby allowing the base material to be folded over the teeth of a user such that the base material abuts both the front and back of the user's teeth; and
    at least one surface feature formed on the base material for providing a deliverable material to a user, said surface feature dissolving or absorbing into the user's body upon use.

* * * * *